United States Patent
LaRosa et al.

(10) Patent No.: US 11,766,445 B2
(45) Date of Patent: Sep. 26, 2023

(54) ORAL SOFT GEL CAPSULE CONTAINING PSYCHEDELIC COMPOUND

(71) Applicant: Concept Matrix Solutions, Newbury Park, CA (US)

(72) Inventors: Tony LaRosa, Woodland Hills, CA (US); Robert Davidson, Woodland Hills, CA (US); David Reid, Woodland Hills, CA (US)

( * ) Notice: Subject to any disclaimer, the term of this patent is extended or adjusted under 35 U.S.C. 154(b) by 45 days.

(21) Appl. No.: 16/947,003

(22) Filed: Jul. 14, 2020

(65) Prior Publication Data

US 2021/0015833 A1  Jan. 21, 2021

Related U.S. Application Data

(60) Provisional application No. 62/875,580, filed on Jul. 18, 2019.

(51) Int. Cl.
| | |
|---|---|
| *A61K 31/675* | (2006.01) |
| *A61K 9/48* | (2006.01) |
| *A61K 31/4045* | (2006.01) |

(52) U.S. Cl.
CPC .......... *A61K 31/675* (2013.01); *A61K 9/4825* (2013.01); *A61K 9/4866* (2013.01); *A61K 31/4045* (2013.01)

(58) Field of Classification Search
CPC .. A61K 31/675; A61K 9/4825; A61K 9/4866; A61K 31/4045
See application file for complete search history.

(56) References Cited

U.S. PATENT DOCUMENTS

| | | | | |
|---|---|---|---|---|
| 6,214,376 B1* | 4/2001 | Gennadios | ............ | A61K 9/4816 424/452 |
| 2012/0108510 A1* | 5/2012 | Young | .................. | A61K 31/506 514/10.7 |
| 2012/0277323 A1* | 11/2012 | Kumar | .................. | A61K 31/135 536/99 |
| 2018/0221396 A1* | 8/2018 | Chadeayne | ........ | A61K 31/4045 |
| 2020/0147038 A1* | 5/2020 | Russ | ...................... | A61K 31/65 |

FOREIGN PATENT DOCUMENTS

WO  WO-2018195455 A1 * 10/2018 ........... A61K 31/135

OTHER PUBLICATIONS

Natural Products Insider ([retrieved from on-line website: https://www.naturalproductsinsider.com/specialty-nutrients/softgels-are-shell-game, 2012, pp. 1-4]) (Year: 2102).*
Natural Products Insider ([retrieved from on-line website: Https://www.naturalproductsinsider.com/specialty-nutrients/softgels-are-shell-game, 2012, pp. 104]) (Year: 2012).*
Natural Products Insider ([https://www.naturalproductsinsider.com/specialty-nutrients/softgels-are-shell-game], 2012, pp. 1-5) (Year: 2012).*

* cited by examiner

*Primary Examiner* — Kyung S Chang

(74) *Attorney, Agent, or Firm* — Carlson, Caspers, Vandenburgh & Lindquist, P.A.

(57) ABSTRACT

Provided is an oral soft gel capsule that includes a psychedelic compound. Also provided is a method of treating in a subject a disease or disorder ameliorated by a psychedelic compound, that includes orally administering to a subject an oral soft gel capsule that includes a therapeutically effective amount of the psychedelic compound. Also provided is a method of orally administering to a subject an oral soft gel capsule that includes a therapeutically effective amount of the psychedelic compound. Also provided is a method of orally administering to a subject an oral soft gel capsule that includes a low dose (e.g., microdose or sub-therapeutic dose) of the psychedelic compound.

26 Claims, No Drawings

ORAL SOFT GEL CAPSULE CONTAINING PSYCHEDELIC COMPOUND

RELATED U.S. APPLICATION DATA

This application claims priority to provisional patent application No. 62/875,580 filed on Jul. 18, 2019, the contents of which are incorporated by reference herein in its entirety.

SUMMARY

The present invention provides for an oral soft gel capsule that includes: (i) a soft capsule shell; (ii) psychedelic compound selected from the group consisting of psilocybin, psilocin, mescaline, Lysergic acid diethylamide (LSD), ketamine, salvinorin A, ibotenic acid, muscimol, N,N-dimethyltryptamine (DMT), 3,4-Methylenedioxymethamphetamine (MDMA), methyl diethanolamine, also known as N-methyl diethanolamine (MDEA), 3,4-methylenedioxyamphetamine (MDA), and combinations thereof; and (iii) liquid vehicle compatible with the capsule shell, and effectively dissolves and/or suspends the psychedelic compound.

The present invention also provides for a method of treating in a subject a disease or disorder ameliorated by a psychedelic compound. The method includes orally administering to the subject an oral soft gel capsule described herein, in an amount and for a period of time sufficient to effectively treat the disease or disorder.

The present invention also provides for a method of treating in a subject a psychological or neurological disorder. The method includes orally administering to the subject an oral soft gel capsule described herein, in an amount and for a period of time sufficient to effectively treat the psychological or neurological disorder.

The present invention also provides for a method of treating in a subject at least one of obsessive compulsive disorder (OCD), depression, pain, irritability, fibromyalgia, post-traumatic stress disorder (PTSD), cluster headaches, paranoia, psychosis, anxiety, panic attacks, flashbacks, smoking addiction, alcohol addiction, drug addiction, and cocaine addiction. The method includes orally administering to the subject an oral soft gel capsule described herein, in an amount and for a period of time sufficient to effectively treat the disease or disorder.

The present invention also provides for a method of improving creativity, boosting physical energy level, attaining emotional balance, improving the mood, and/or increasing performance on problems-solving tasks. The method includes orally administering to the subject an oral soft gel capsule described herein, in an amount and for a period of time sufficient to effectively improve creativity, boost physical energy level, attain emotional balance, improve the mood, and/or increase performance on problems-solving tasks.

The present invention also provides for a method of orally administering to a subject an oral soft gel capsule described herein, wherein the oral soft gel capsule includes a low dose or microdose of the psychedelic compound.

The present invention also provides for a method of administering to a subject a low dose or microdose of a psychedelic compound. The method includes orally administering an oral soft gel capsule described herein, wherein the oral soft gel capsule includes a low dose or microdose of the psychedelic compound.

DETAILED DESCRIPTION

The present invention is directed to an oral soft gel capsule that includes a psychedelic compound. The present invention is also directed to a method of treating in a subject a disease or disorder ameliorated by a psychedelic compound, that includes orally administering to a subject an oral soft gel capsule that includes a therapeutically effective amount of the psychedelic compound. The present invention is also directed to a method of orally administering to a subject an oral soft gel capsule that includes a therapeutically effective amount of the psychedelic compound. The present invention is also directed to a method of orally administering to a subject an oral soft gel capsule that includes a low dose (e.g., microdose or sub-therapeutic dose) of the psychedelic compound.

Definitions:

The term "subject" refers to living organisms such as humans, dogs, cats, and other mammals. Administration of the medicaments included in the oral softgel capsules of the present invention can be carried out at dosages and for periods of time effective for the treatment of the subject. In some embodiments, the subject is a human. Unless otherwise specified, the human subject can be a male or female, and can further be an adult, adolescent, child, toddler, or infant.

The term "enteral administration" refers to a drug administration via the human gastrointestinal tract. Enteral administration involves the esophagus, stomach, and small and large intestines (i.e., the gastrointestinal tract). Methods of administration include oral and rectal. Enteral administration may be divided into three different categories, depending on the entrance point into the GI tract: oral (by mouth), gastric (through the stomach), and rectal (from the rectum). (Gastric introduction involves the use of a tube through the nasal passage (NG tube) or a tube in the belly leading directly to the stomach (PEG tube). Rectal administration usually involves rectal suppositories.) Enteral medications come in various forms, including, e.g., tablets to swallow, chew or dissolve in water; capsules and chewable capsules (with a coating that dissolves in the stomach or bowel to release the medication there), oral soluble films, time-release or sustained-release tablets and capsules (which release the medication gradually), osmotic delivery systems, powders or granules, and liquid medications or syrups.

The term "oral administration" refers to a route of administration where a substance is taken through the mouth. Many medications are taken orally because they are intended to have a systemic effect, reaching different parts of the body via the bloodstream.

The term "pharmaceutically acceptable" refers to those compounds, excipients, active ingredients, materials, compositions, and/or dosage forms that are, within the scope of sound medical judgment, suitable for use in contact with the tissues of human beings and animals without excessive toxicity, irritation, allergic response, or other problems or complications commensurate with a reasonable benefit/risk ratio.

The term "aggregate" refers to the total formed, calculated, or obtained by the combination of separate units or items.

Capsule

The term "capsule" refers to a generally safe, readily dissolvable enclosure for carrying certain pharmaceutical formulations. Capsules include a shell surrounding and containing the pharmaceutical formulation. The capsule prevents degradation of the pharmaceutical formulation and allows for storage for a period of several months at room temperature. The capsule is adapted for self-administration by an individual. The capsule shell dissolves or disintegrates in the digestive tract after the capsule is ingested, thereby releasing the pharmaceutical formulation to be absorbed by the body of the individual ingesting the capsule.

Capsule Shells

Capsule shells are typically made of either animal based or plant based components that readily dissolve or disintegrate after ingestion. Animal based components may include gelatin manufactured from the collagen of animal skin and/or bone. In certain embodiments, capsule is made of gelatin. Other suitable matrix substances such as total synthetic polymer chemicals having gelatin-like properties may be used to manufacture the capsules. Plant based components may include vegetable starch, cellulose, hypromellose (a polymer formulated from cellulose) or pullulan (polysaccharide polymer produced from tapioca starch). In some embodiments, plant based components may include carrageenan, potato starch, cassava starch, cornstarch, arrowroot or combinations thereof. The composition, manufacture, and use of capsule shells are well known in the art.

Softgel

In certain embodiments, the capsule is a softgel capsule, also referred to herein, as "soft gel" capsule. Softgel capsules are particularly suitable for containing liquid-based ingredients, such as pharmaceutical ingredients dissolved, dispersed, and/or suspended in a liquid vehicle. Softgel capsules also possess particular advantages for substances which require total protection from air and light, because the gelatin is completely sealed around the contents. For example, the softgel capsule can block a significant amount (e.g., at least 90%, at least 99%, or up to 100%) of UV light from transmitting therethrough.

One advantage of softgel capsules is the improved rate and extent of absorption, and the reduced variability per dosage, particularly for water soluble pharmaceutical agents. Another advantage of softgel capsules is that they are substantially easier to swallow than, for example, tablets or hard-shell capsules. Yet another advantage is the absence of poor taste, aftertaste, sharp edges or other sensory problems associated with alternatives such as tablets or hard-shell capsules. Another advantage is an improved patient compliance compared to tablets and hard-shell capsules.

Another advantage is the ease and convenience of orally administering pharmaceuticals that have to be formulated in liquid dosage form. Yet another advantage is the improved ability to control the exact amount of a liquid pharmaceutical agent compared to a solid or powder form. Another advantage is their resistance to tampering and/or altering the dosage after formulation and before administration. Yet another advantage is that the active pharmaceutical agent is hermetically sealed.

Another advantage is the improved homogeneity of the formulation compared to a tablet, granules or powder formulation. Yet another advantage is the enhanced stability of the pharmaceutical agent in the softgel capsule. Another advantage is the ease of storage and increased shelf life of the softgel capsule compared to hard-shell capsules. Yet another advantage is the rapid disintegration of the softgel capsule upon administration leading to enhanced rate of absorption of the pharmaceutical agent, and thereby, an improved rate of therapeutic effect compared to, for example, tablets. Another advantage is the substantially decreased plasma variability of the drug, thereby leading to an enhanced level of bioavailability upon administration compared to tablets and hard-shell capsules.

The shell of a softgel capsule is typically made of animal based components such as gelatin combined with a plasticizer such as glycerin and a solvent such as water. In some embodiments, plant based components such as cellulose, hypromellose, vegetable starch, tapioca starch, carrageenan, potato starch, cassava starch, cornstarch, arrowroot or combinations thereof may be used in place of gelatin to make vegetarian softgel capsules. Other animal based or plant based components with properties similar to gelatin or starch that are suitable for polymerization or activated crosslinking may also be used. Softgel capsule shells are typically made and filled with pharmaceutical formulations in continuous processes that are known in the art.

The term "plasticizer" refers to a substance that is added to the gelatin or starch to form the softgel capsule. Plasticizers may include glycerin, sorbitol, propylene glycol, other suitable polyols, or combinations thereof. The amount of plasticizer can be adjusted to arrive at softgel shells with the desired level of softness and flexibility. Some embodiments may include from about 30 to about 50% by weight gelatin; at least 18% by weight, and preferably up to about 40% by weight, of a plasticizer; and from about 20 to about 50% by weight water. These formulations, when formed into capsules and dried, will result in softgel capsules containing from about 40 to about 75% by weight gelatin; from about 18% to about 40% by weight plasticizer; and from about 5 to about 15% by weight water. In certain embodiments a weight ratio of 10:3:12 of the gelatin, plasticizer and solvent may be used. The softgel shells may be prepared by combining appropriate amounts of gelatin, water, plasticizer, and any optional components in a suitable vessel and agitating and/or stirring while heating to about 65° C. until a uniform solution is obtained.

In some embodiments, the softgel shells include a layer or coating. The coating may include a film coating or an enteric resistant coating that allows for controlled release, delayed release or sustained release of the contents of the capsule upon administration. In certain embodiments, the softgel shells are coated with cellulose acetate phthalate (CAP).

The term "preservative" refers to compounds which are used to prevent the growth of bacteria, fungi, mold and other microbes. They are used for their individual antibacterial (destroying and inhibiting the growth of bacteria), antifungal (destroying and inhibiting the growth of fungus), anti-microbial, anti-mycoplasmal, anti-viral and/or anti-prion properties. Suitable preservatives can include, but are not limited to, at least one of a benzalkonium chloride, a benzethonium chloride, a chlorohexidine, a phenol, a m-cresol, a benzyl alcohol, an alkyl paraben (methylparaben, ethylparaben, propylparaben, butylparaben, and the like), sodium dehydroacetate, an o-cresol, a p-cresol, a chlorocresol, a phenylmercuric nitrate, a thimerosal, a benzoic acid and any mixture thereof of one or more preservatives. See, e.g., Wallhauser, K., Develop. Biol. Standard. 24, pp. 9-28 (Basel, S. Krager, 1974. In some embodiments, the soft gelatin shells may contain a preservative to prevent the growth of fungi. In certain embodiments, preservatives may include the parabens, such as methylparaben, propylparaben, isopropylparaben, butylparaben, and isobutylparaben, and their salts such as sodium butylparaben, benzoic acid and its salts and esters, benzyl alcohol, urea derivatives such as diazofidinyl urea, imidazolidinyl urea, and DMDM hydantoin, sorbic acid and its salts, and the like. Various preferred embodiments may include preservatives such as methyl- and propylparabens and sorbic acid. Some embodiments may include about 0.2 wt. % of preservative mixed with the gelatin mass of the softgel. Certain embodiments may include about 4:1 ratio of methylparaben and propylparaben as preservatives. In various embodiments, the preservative may be absent.

The term "opacifier" refers to an agent or a mixture of agents which when added to a preparation make the ensuing system opaque. Representative opacifier agents include, but are not limited to, pharmaceutically acceptable metal oxides, especially titanium dioxide. Certain embodiments may include about 0.2 wt. % to about 1.2 wt. % of opacifier mixed with the gelatin mass of the softgel. In some embodiments, the opacifier may be absent.

The term "flavorant" refers to a compound that provides a desired taste and/or smell. The flavorant can be a natural or artificial compound, and it can, but does not have to be, oil-soluble. Flavorants include isoamyl acetate (or other banana flavorant), benzaldehyde (or other almond flavorant), cinnamic aldehyde (or other cinnamon flavorant), citric acid or ethyl propionate (or other fruity flavorant), methyl anthranilate (or other grape flavorant), limonene (or other orange flavorant), ethyl decadienoate (or other pear flavorant), allyl hexanoate (or other pineapple flavorant), ethyl maltol (or other sugar or cotton candy flavorant), ethylvanillin (or other vanilla flavorant), methyl salicylate (or other wintergreen flavorant), glyceryl monoacetate (E1516 food additive), glyceryl diacetate (E1517 food additive), and combinations thereof. Some embodiments may include about 0.1 wt. % to about 2 wt. % of flavorant.

The term "colorant" refers to compositions or compounds, such as, but not limited to, pigments, dyes and tints, which impart color. Typical colorants may include, carotenoids (E160, E161, E164), chlorophyllin (E140, E141), anthocyanins (E163), and betanin (E162). Other colorants such as, annatto (E160b), a reddish-orange dye made from the seed of the achiote, caramel coloring (E150a-d), made from caramelized sugar, carmine (E120), a red dye derived from the cochineal insect, *Dactylopius coccus*, elderberry juice (E163), lycopene (E160d), paprika (E160c), and turmeric (E100) may also be used.

The term "excipient" as used herein includes, but is not limited to, preservative, plasticizer, opacifier, colorant and flavorant as described above, or any combination thereof. The term excipient may also include a solvent, binder, surfactant, emulsifier, wetting agent, suspending agent, or any combination thereof. Suitable excipients or additives that can be used in the formulation of softgel capsules are described in, e.g., Lachman, et al., "The Theory and Practice of Industrial Pharmacy," 4th Edition (2013); Rowe et al., "Handbook of Pharmaceutical Excipients," 8th Edition (2017); and Remington, "The Science and Practice of Pharmacy," 22nd Edition (2015). From the regulatory perspectives, all excipients and additives used in the formulation of the softgel capsules described herein should preferably be approved for use in oral pharmaceutical dosage forms.

Liquid Vehicle

The softgel shell of the capsules is filled with a pharmaceutical formulation. Typically, the pharmaceutical formulation includes a pharmaceutical ingredients mixed, dissolved, dispersed, suspended, or emulsified with a liquid vehicle. The characteristics of the liquid vehicle may be hydrophilic or lipophilic. In certain embodiments, the liquid vehicle may include a combination of hydrophilic and lipophilic materials. In various embodiments, the hydrophilic materials, lipophilic materials, or combinations thereof, are encapsulated within the softgel shell in the form of a preconcentrate. In some embodiments, the preconcentrate further includes one or more surfactants. In certain embodiments, the ingredients of the liquid vehicle are present in the form of emulsions either before, during or after oral administration of the softgel capsules. In various embodiments, the emulsions include microemulsions, nanoemulsions and combinations thereof.

In some embodiments, the liquid vehicle may include one or more oils such as silicone oil, vegetable oil, glycerin, hydrogenated vegetable oil, lecithin, beeswax, tochopherols, polyethylene glycols (e.g., PEG 200, 300, 400 or 600), polyoxyethylene-polyoxypropylene copolymers (poloxamers), propylene glycol, Miglyol® 812 (neutral oil, triglycerides of medium chain fatty acids), omega oil, soybean oil, canola oil, sunflower oil, macadamia oil, peanut oil, grapeseed oil, pumpkin seed oil, linseed oil, flaxseed oil, olive oil, maize oil, safflower oil, sesame oil, pine kernel oil, conjugated linoleic acid, almond oil, peach kernel oil, apricot kernel oil, walnut oil, rapeseed oil, raspberry seed oil, bilberry seed oil, cranberry seed oil, pomegranate seed oil and other fruit seed oils, seabuckthorn oil, chia oil, perilla oil, diaglycerol (DAG) oil, vegetable derived sources of omega 3, fermented sources of eicosapentaenoic acid (EPA), fermented sources of docosahexaenoic acid (DHA), fermented sources of a combination of EPA, DHA and other omega 3s, including fish oil and hill oil, sources of gamma-linolenic acid (GLA) or stearidonic acid (SA), fractionated coconut oil, and combinations thereof. Sources of DHA, EPA and alpha-linoleic acid (ALA) include, but are not limited to, fish oils, yeasts or other microorganisms or monocellular sources and vegetable oils, primarily flaxseed, soy, and canola. Sources of GLA include, but are not limited to, evening primrose oil, blackcurrent seed oil, borage oil, and echium oil.

The term "silicone oil" refers to a liquid siloxane-containing polymer. Suitable silicone oils may include polyalkyl siloxanes and polyalkyl phenyl siloxanes, having dynamic viscosities between less than 1 to as great as $10^7$ centistokes at 25° C. Suitable low viscosity silicone oils are the cyclic polymers of dimethylsiloxane containing from three to six (typically four or five) siloxane units in the ring, commonly referred to as cyclomethicone. Various cyclomethicones are available, having different proportions of the trimer, tetramer, pentamer, and hexamer components. Other suitable low viscosity silicone oils include the lower polydimethylsiloxanes (dimethicones), such as hexamethyldisiloxane, and lower polyalkylphenylsiloxanes, such as phenyldimethicones. Other suitable silicone oils include dimethiconol, dimethicone copolyol, laurylmethicone, laurylmethicone copolyol, cetyl dimethicone copolyol, and the like. Examples include Dow Corning 200 (dimethicone, available in various viscosities), 244, 245, 344, and 345 (cyclomethicone), Q2-5200 (lauryl dimethicone copolyol), 3225C (cyclomethicone and dimethicone copolyol), 1401 (cyclomethicone and dimethiconol), 1403 (dimethicone and dimethiconol), and Abil WE09 (polyglycerol-4 isostearate/cetyl dimethicone copolyol/hexyl laurate and combinations thereof.

Preferred embodiments include vegetable oil, glycerin, hydrogenated vegetable oil, lecithin, beeswax, tochopherols, polyethylene glycols (e.g., PEG 400, PEG 600), polyoxyethylene-polyoxypropylene copolymers (poloxamers), propylene glycol, and Miglyol® 812 (neutral oil, triglycerides of medium chain fatty acids). In specific embodiments, the liquid vehicle does not include dimethyl isosorbide, surfactants, diethylene glycol monoethyl ether, water, or alcohol.

In specific embodiments, the oral soft gel capsule contains a liquid vehicle which has softgel(s), granules, tablet(s), and/or pellet(s) suspended therein. In this dosage form, tablets, granules, pellets and/or capsules can be placed inside a large, soft gelatin capsule. The dosage form allows for different configurations for fixed-dose combinations, such as a softgel within a softgel, one or two tablets within a softgel, granules within a softgel, or any combination of these to address challenges of multi-active formulations. This delivery system allows for single or multiple active ingredients with different release profiles, multiple active ingredients where at least one is a liquid or semi-solid, offering unique options for nutraceutical products.

Methods of Manufacturing Softgel Capsules

Softgel capsules and encapsulation methods are generally known in the art and are described, e.g., in P. K. Wilkinson et al., "Softgels: Manufacturing Considerations", Drugs and the Pharmaceutical Sciences, 41 (Specialized Drug Delivery Systems), P. Tyle, Ed. (Marcel Dekker, Inc., New York, 1990) pp. 409-449; F. S. Hom et al., "Capsules, Soft" Encyclopedia of Pharmaceutical Technology, vol. 2, J. Swarbrick and J. C. Boylan, eds. (Marcel Dekker, Inc., New York, 1990) pp. 269-284; M. S. Patel et al., "Advances in Softgel Formulation Technology", Manufacturing Chemist, vol. 60, no. 7, pp. 26-28 (July 1989); M. S. Patel et al., "Softgel Technology", Manufacturing Chemist, vol. 60, no. 8, pp. 47-49 (August 1989); R. F. Jimerson, "Softgel (Soft Gelatin Capsule) Update", Drug Development and Industrial Pharmacy (Interphex 86 Conference), vol. 12, no. 8 & 9, pp. 1133-1144 (1986); and W. R. Ebert, "Soft Elastic Gelatin Capsules: A Unique Dosage Form", Pharmaceutical Technology, vol. 1, no. 5, pp. 44-50 (1977).

Softgel capsules of the disclosure may be manufactured using a variety of commercial manufacturing processes including, but not limited to, plate process, rotary die process, reciprocating die process, accogel process, seamless gelatin capsule process, combinations thereof, or other processes known in the art.

In an exemplary embodiment, a mixture of gelatin, plasticizer and water is heated to an elevated mixing temperature under homogenous mixing conditions. The mixing temperature may be at least 94° C. and may be between about 94 and about 98° C. The mixing conditions facilitate effective heat transfer and homogenization of a highly viscous mixture and may include blending the mixture with a combination of laminar and turbulent flow with forced axial flow. A combination of various mixing forces may facilitate mixing a highly viscous mixture and maintaining effective thermal heat conduction within the mixture. A Unimix SRA 700 SO mixing apparatus by Ekato may provide a suitable level of homogenization of a highly viscous mixture of gelatin and plasticizer in water.

Once the mixture is heated to the mixing temperature, mixing is maintained for even thermal distribution throughout the mixture, and then may be dropped to a lower maintenance temperature to maintain the mixture in a homogenous liquid state. The maintenance temperature may be between about 75 and about 85° C. Once homogenized, the mixture may be extended out across a large surface area to solidify into sheets of gelatin and water upon cooling.

The Bloom or gel strength of gelatin is a measure of the cohesive strength of the crosslinking that occurs between gelatin molecules and is proportional to the molecular weight of the gelatin. Bloom may vary based on desired properties but ranges from 150 to 250 g.

Viscosity of gelatin, is a measure of the molecular chain length and determines the manufacturing characteristics of the gelatin film. The viscosity for gelatin can range from 25 to 45 millipoise. The plasticizers can be used with gelatin in soft capsule manufacture. Glycerin USP, Sorbitol USP, Pharmaceutical Grade Sorbitol Special, and combinations of these are the most prevalent.

The maximum capsule size and shape for convenient oral use in humans is the 20 minim oblong, the 16 minim oval, or the 9 minim round. A minim is equivalent to the amount of water in a drop, which is also equal to one grain. The sealing temperature of the gelatin films is usually in the range of 37 to 40° C. preparations for encapsulation should have a pH between 2.5 and 7.5.

For oral products, the medicament may have sufficient solubility in the solvent system so that the necessary dose is contained in a liquid vehicle with a maximum fill volume of 16 to 20 minims (1 to 1.25 cc).

Pharmaceutical ingredients that are organic or inorganic solids may be capsulated. Such materials should be 80 mesh or finer in particle size, owing to certain close tolerances of the capsulation equipment and for maximum homogeneity of the suspension. One laboratory tool for this purpose is known as the "base adsorption" of the solid(s) to be suspended. Base adsorption is expressed as the number of grams of liquid base required to produce a capsulable mixture when mixed with one gram of solid(s). The base adsorption of a solid is influenced by such factors as the solid's particle size and shape, its physical state (fibrous, amorphous, or crystalline), its density, its moisture content, and its oleophilic or hydrophilic nature.

In the determination of base adsorption, the solid(s) may be completely wetted by the liquid vehicle. For glycol and nonionic type vehicles, the addition of a wetting agent is seldom included, but for vegetable oils, complete wetting of the solid(s) may include an additive. In preferred embodiments, soy lecithin, at a concentration of 2 to 3% by weight of the oil, serves for this purpose, and is universally accepted for food and drug use.

The final formulation of a suspension invariably includes a suspending agent to prevent the settling of the solids and to maintain homogeneity prior to, during, and after capsulation.

In preferred embodiments, suspending agent may include a wax mixture, the polyethylene glycols 4000 and 6000.

In a typical commercial manufacturing process, the gelatin is weighed on printomatic scales and mixed with the accurately metered (printomatic) and chilled (7° C.) liquid constituents in suitable equipment, such as a Pony Mixer. The resultant fluffy mass is transferred to melting tanks and melted under vacuum (29.9" Hg); at 93° C. The mixing process generally takes about 25 min for 270 kg of mass, and the melting procedure generally takes about 3 hours. A sample of the resulting fluid mass is visually compared with a color standard, and additional colorants are blended into the mass if adjustments are desired. The mass is then maintained at a temperature of 57 to 60° C. before and during the capsulation process.

The next steps involve processing in a weigh-off and mixing area containing the necessary equipment and facilities for the preparation of the variety of mixtures that may be capsulated. Typical equipment would include printomatic scales for exacting measurements and control records; stainless-steel jacketed tanks for handling from 10- to 450-gallon batches of mix; and mixers, such as the Cowles, for the initial blending of solids with the liquid base. After the initial blending is completed, the mixture is put through a milling or homogenizing process, using equipment such as the homoloid mill, stone mill, hopper mill, or the Urschel Comitrol. The purpose of the milling operation is not to reduce particle size, but to break up agglomerates of solids and to make certain that all solids are "wet" with the liquid vehicle, so as to achieve a smooth and homogenous mixture.

Following the milling operation, all mixtures are subjected to deaeration, and particularly so if the capsulation machine is equipped with a positive displacement pump. Deaeration allows the mixtures to achieve uniform capsule fill weights; it also protects against loss of potency through oxidation prior to and during capsulation. When small amounts of volatile ingredients are included in a formulation, they are carefully added and blended into the bulk mixture after deaeration. Most liquids and suspensions may be deaerated by means of equipment designed to expose thin layers of the material continuously to a vacuum (29.5" Hg) and at the same time transfer the material from the mixing tank to the container that will be used at the capsulation machine. Suspensions or liquid mixtures containing volatile liquids or liquid surface active agents as chief constituents of the formula may be deaerated by subjection to temperatures up to 60° C. for the period suitable to achieve the results desired. After deaeration, the mixture is ready to be capsulated.

At this point, samples of the mixture may be sent to the quality control laboratory for various tests, such as ingredient assays and specific gravity, and tests for homogeneity of suspension, moisture content, or air entrapment.

The gelatin mass is fed by gravity to a metering device (spreader box), which controls the flow of the mass onto air cooled (13 to 14° C.) rotating drums. Gelatin ribbons of controlled (±10%) thickness are formed. The wet shell thickness may vary from 0.022 to 0.045 inch, but for most capsules, it is between 0.025 and 0.032 inch. Thicker shells may be used to provide suitably greater structural strength.

In the subsequent step, the ribbons are fed through a mineral oil lubricating bath, over guide rolls, and then down between the wedge and the die rolls. The material to be capsulated flows by gravity into a positive displacement pump. The pump accurately meters the material through the leads and wedge and into the gelatin ribbons between the die rolls. The bottom of the wedge contains small orifices lined up with the die pockets of the die rolls. The capsule is about half sealed when the pressure of the pumped material forces the gelatin into the die pockets, where the capsules are simultaneously filled, shaped, hermetically sealed, and cut from the gelatin ribbon. The sealing of the capsule can be achieved by mechanical pressure on the die rolls and the heating (37 to 40° C.) of the ribbons by the wedge.

During manufacture, capsule samples may be taken periodically for seal thickness and fill weight checks. The seals are measured under a microscope, and changes in ribbon thickness, heat, or die pressure are made if necessary. Acceptable seal thickness is generally one half to two thirds of the ribbon thickness. Fill weight checks may be made by weighing the whole fresh capsule, slitting it open, and expressing the contents. The shell is then washed in a suitable solvent (petroleum ether), and the empty shell is reweighed. If necessary, adjustments in the pump stroke can be made to obtain the proper fill weight.

Immediately after manufacture, the capsules may be automatically conveyed through a naphtha wash unit to remove the mineral oil lubricant. The washed capsules may be automatically subjected to a preliminary infrared drying step, which removes 60 to 70% of the water as desired, or may be manually spread directly on trays. Capsules from the infrared dryer are also spread on trays, and all capsules may be allowed to come to equilibrium with forced air conditions of 20 to 30% relative humidity at 21 to 24° C.

Capsules at equilibrium with a relative humidity (RH) of about 20 to 30% at 21 to 24° C. may be considered "dry," and the shell of such a capsule may contain 6 to 10% water, depending on the gelatin formula used. The moisture content of the shell may be determined by the toluene distillation method, collecting the distillate over a period of one hour. Additional water may be removed from "dry" capsules by further heating, e.g., at 40° C.

After drying, the capsules may be transferred to the inspection department and held until released by the quality control department. The inspection and quality control steps in the processing of capsules generally conform to good manufacturing practice. Control tests specifically applicable to the quality of soft gelatin capsules may involve seal thickness determinations, total or shell moisture tests, capsule fragility or rupture tests, and the determination of freezing and high temperature effects.

In another exemplary embodiment, a pump delivers the warm gelatin over two chilled drums located at mutually opposite sides of a rotary die machine, through a spreader box that sits over each drum. The warm liquid gelatin flows over the drums and the cooling transforms the liquid gelatin into two solid ribbons of gel. The left and right ribbons pass over rollers which feed them through two die rolls. The die rolls determine the shape and size of softgels and cut the softgel shell from the ribbons as they turn around.

Simultaneously, a sensitive and high accuracy positive displacement pump delivers the fill material or liquid vehicle into a heated wedge which sits between rotary dies. The wedge injects the liquid vehicle into the die cavities between ribbons just before the die rolls cut the ribbons and seal the two halves together to form warm softgel capsules. The just formed softgel capsules may slide gently through a chute onto a conveyor belt which carries them to the tumble dryer where cooling and drying process takes place.

Typically, soft encapsulation machines form at least two flexible gelatin sheets or ribbons by cooling molten gelatin on separate drums then lubricating and guiding the sheets into communication with each other over co-acting dies while simultaneously dispensing a desired quantity of liquid vehicle between the sheets in sync with cavities in the outer surfaces of the dies to produce softgel capsules. The encapsulation machines typically utilize gearing to control the relative rotations of the various components and fill mechanisms to synchronize the operation of these various components. The synchronization of these various components, however, can vary depending upon a variety of factors, such as the dies used, the number of cavities and the size of the cavities on the dies, and the type of material used to form the sheets. To change the synchronization of the various components, mechanical gears may be changed to obtain the desired ratios and synchronization of these components. Additionally, the use of mechanical gears provides finite gear ratios which limit the synchronization of the various components to the mechanical gears that are available. Thus, it would be advantageous to provide a capsule machine wherein the synchronization and rates at which the various components operate can be altered without the necessity of changing gears. Additionally, it would be advantageous to allow various components, such as the fill mechanism, to be adjusted independently of the other components while the machine is running to allow for adjustments of the timing of fill material or liquid vehicle inserted into each of the soft capsules. It would also be advantageous to eliminate the use of casting drums in the making of softgel capsules.

During the operation of the capsule making machine, the contact between the adjacent dies can be adjusted by the operator of the capsule making machine. Typically, the operator may move one of the dies closer to the other die so that the pressure or force exerted on the sheets passing between the adjacent dies can be adjusted. The operator may adjust the pneumatic pressure thereby altering the force the dies exert on one another and on the sheets. This adjustability allows an operator to customize the pressure to ensure that quality softgel capsules are produced. It would be advantageous to monitor/record the pressure applied to the dies so that quality capsules are produced without inducing excessive wear or premature wear on the dies.

A material fill mechanism is used to supply the liquid vehicle that is encapsulated within the soft capsules. The fill mechanism includes a plurality of positive displacement plunger-type pumps that are arranged in a housing above the dies. The plunger-type pumps are positioned on a yoke that moves linearly in a reciprocating motion to allow the plunger-type pump to fill with the liquid fill material or liquid vehicle on one stroke and subsequently discharge the liquid vehicle on the other stroke. A valving arrangement between opposing pumps is utilized to control the discharge and filling of the pumps. The valve arrangement includes a sliding member that moves linearly back and forth in a direction generally perpendicular to the linear motion of the yoke. The discharge of the liquid vehicle into the sheets as they are passing through the dies is coordinated with the operation of the dies to ensure that the timing of the injection of the liquid vehicle is synchronized with the cavities on the dies. Typically, this synchronization may be performed through the use of mechanical gears that link the timing of the stroke to the rotation of the dies.

The sliding member of the valving mechanism may be lubricated. Typically, the lubrication is provided by a lubricating pump with its own separate drive. It would be advantageous if a motion of the slide member and/or the yoke could be utilized to drive the lubrication pump. The pumps are typically contained within a housing that is filled with a lubricating oil that is used to lubricate the sliding member.

The pumps are typically driven by a drive mechanism that is also located within the pump housing. When switching from one liquid vehicle to another, the pump and all of the components in the pump housing may be thoroughly cleaned to remove any contamination. The location of the drive mechanism within the pump housing provides additional components that may also be cleaned when changing the liquid vehicle. The softgel capsules produced by the encapsulation machine may be transported from the encapsulation machine to a dryer to additionally dry the softgel capsules and to make them into final form.

The softgel capsules manufactured using any of the processes described above may be subjected to a variety of quality control tests including, but not limited to, disintegration test, dissolution test, weight variation test, content uniformity test, capsule stability test, combinations thereof, or other tests known in the art.

Specific Ranges, Values, and Embodiments

The specific embodiments describing the ranges and values provided below are for illustration purposes only, and do not otherwise limit the scope of the disclosed subject matter, as defined by the claims.

In specific embodiments, the psychedelic compound is selected from the group consisting of psilocybin, psilocin, baeocystin, mescaline, LSD, ketamine, salvinorin A, ibotenic acid, muscimol, DMT, MDMA, MDEA, MDA, and combinations thereof.

In specific embodiments, the psychedelic compound is at least one of psilocybin, psilocin and baeocystin.

In specific embodiments, the psychedelic compound is obtained from the genera *Copelandia, Gymnopilus, Inocybe, Mycena, Panaeolus, Pholiotina, Pluteus,* or *Psilocybe.*

In specific embodiments, the psychedelic compound is present as an extract obtained from the genera *Copelandia, Gymnopilus, Inocybe, Mycena, Panaeolus, Pholiotina, Pluteus,* or *Psilocybe.*

In specific embodiments, the psychedelic compound is present as a purified extract obtained from the genera *Copelandia, Gymnopilus, Inocybe, Mycena, Panaeolus, Pholiotina, Pluteus,* or *Psilocybe.*

In specific embodiments, the psychedelic compound is at least one of psilocybin, psilocin and baeocystin, obtained from the genera *Copelandia, Gymnopilus, Inocybe, Mycena, Panaeolus, Pholiotina, Pluteus,* or *Psilocybe.*

In specific embodiments, the psychedelic compound is at least one of psilocybin, psilocin and baeocystin, obtained as an extract from mushrooms.

In specific embodiments, the psychedelic compound is at least one of psilocybin, psilocin and baeocystin, synthetically prepared.

In specific embodiments, the psychedelic compound is present in up to 200 mg.

In specific embodiments, the psychedelic compound is present in up to 150 mg.

In specific embodiments, the psychedelic compound is present in up to 100 mg.

In specific embodiments, the psychedelic compound is present in up to 50 mg.

In specific embodiments, the psychedelic compound is present in up to 25 mg.

In specific embodiments, the psychedelic compound is present in up to 10 mg.

In specific embodiments, the psychedelic compound is present in up to 5 mg.

In specific embodiments, the psychedelic compound is present in up to 2.5 mg.

In specific embodiments, the psychedelic compound is present in up to 1 mg.

In specific embodiments, the psychedelic compound is present in up to 0.5 mg.

In specific embodiments, the psychedelic compound is present in up to 0.25 mg.

In specific embodiments, the psychedelic compound is present in 1-200 mg.

In specific embodiments, the psychedelic compound is present in 1-150 mg.

In specific embodiments, the psychedelic compound is present in 1-100 mg.

In specific embodiments, the psychedelic compound is present in 1-50 mg.

In specific embodiments, the psychedelic compound is present in 1-25 mg.

In specific embodiments, the psychedelic compound is present in 1-10 mg.

In specific embodiments, the psychedelic compound is present in 0.01-5 mg.

In specific embodiments, the psychedelic compound is present in 0.01-2.5 mg.

In specific embodiments, the psychedelic compound is present in 0.01-1 mg.

In specific embodiments, the psychedelic compound is present in 0.01-0.5 mg.

In specific embodiments, the psychedelic compound is present in 0.01-0.25 mg.

In specific embodiments, the psychedelic compound is present in up to 35 wt. % of the liquid vehicle.

In specific embodiments, the psychedelic compound is present in up to 30 wt. % of the liquid vehicle.

In specific embodiments, the psychedelic compound is present in up to 25 wt. % of the liquid vehicle.

In specific embodiments, the psychedelic compound is present in up to 20 wt. % of the liquid vehicle.

In specific embodiments, the psychedelic compound is present in up to 15 wt. % of the liquid vehicle.

In specific embodiments, the psychedelic compound is present in up to 10 wt. % of the liquid vehicle.

In specific embodiments, the psychedelic compound is present in up to 5 wt. % of the liquid vehicle.

In specific embodiments, the psychedelic compound is present in 0.01-15 wt. % of the liquid vehicle.

In specific embodiments, the psychedelic compound is present in 0.01-10 wt. % of the liquid vehicle.

In specific embodiments, the psychedelic compound is present in 0.01-5 wt. % of the liquid vehicle.

In specific embodiments, the psychedelic compound is present in 0.01-3.5 wt. % of the liquid vehicle.

In specific embodiments, the psychedelic compound is present in 0.01-2.5 wt. % of the liquid vehicle.

In specific embodiments, the psychedelic compound is present in 0.01-1.5 wt. % of the liquid vehicle.

In specific embodiments, the psychedelic compound is present in 0.01-1 wt. % of the liquid vehicle.

In specific embodiments, the psychedelic compound is present in 0.01-0.5 wt. % of the liquid vehicle.

In specific embodiments, the psychedelic compound is present in 0.01-0.25 wt. % of the liquid vehicle.

In specific embodiments, the psychedelic compound has a purity of at least 95 wt. % pure.

In specific embodiments, the psychedelic compound has a purity of at least 97.5 wt. % pure.

In specific embodiments, the psychedelic compound has a purity of at least 98 wt. % pure.

In specific embodiments, the psychedelic compound has a purity of at least 99 wt. % pure.

In specific embodiments, the psychedelic compound has a purity of at least 99.5 wt. % pure.

In specific embodiments, the psychedelic compound is encapsulated in the liquid vehicle.

In specific embodiments, the psychedelic compound is encapsulated in the form of liposomes, micelles, or both.

In specific embodiments, the capsule shell includes gelatin manufactured from the collagen of animal skin and/or bone.

In specific embodiments, the capsule shell includes hypromellose (a polymer formulated from cellulose) or pullulan (polysaccharide polymer produced from tapioca starch).

In specific embodiments, the liquid vehicle includes at least one of: vegetable oil, glycerin, hydrogenated vegetable oil, lecithin, beeswax, tochopherols, polyethylene glycols (e.g., PEG 400, PEG 600), polyoxyethylene-polyoxypropylene copolymers (poloxamers), propylene glycol, and Miglyol® 812 (neutral oil, triglycerides of medium chain fatty acids).

In specific embodiments, the liquid vehicle does not include an appreciable amount of dimethyl isosorbide, surfactants, diethylene glycol monoethyl ether, water, or alcohol.

In specific embodiments, the liquid vehicle does not include an appreciable amount of dimethyl isosorbide, surfactants, diethylene glycol monoethyl ether, water, or alcohol such that any amount of dimethyl isosorbide is no more than 0.1 wt. %, any amount of surfactants is no more than 0.1 wt. %, any amount of diethylene glycol monoethyl ether is no more than 0.1 wt. %, any amount of water is no more than 0.1 wt. %, and any amount of alcohol is no more than 0.1 wt. %.

In specific embodiments, the oral soft gel capsule contains a liquid vehicle which has softgel(s), granules, tablet(s), and/or pellet(s) suspended therein.

In specific embodiments, the oral soft gel capsule is administered to a subject to treat a disease or disorder ameliorated by a psychedelic compound.

In specific embodiments, treating the disease or disorder includes preventing the disease or disorder from occurring.

In specific embodiments, treating the disease or disorder includes curing the disease or disorder.

In specific embodiments, treating the disease or disorder includes healing the disease or disorder.

In specific embodiments, treating the disease or disorder includes alleviating the disease or disorder.

In specific embodiments, treating the disease or disorder includes alleviating one or more symptoms of the disease or disorder.

In specific embodiments, treating the disease or disorder includes relieving the disease or disorder.

In specific embodiments, treating the disease or disorder includes relieving one or more symptoms of the disease or disorder.

In specific embodiments, treating the disease or disorder includes altering the disease or disorder.

In specific embodiments, treating the disease or disorder includes altering one or more symptoms of the disease or disorder.

In specific embodiments, treating the disease or disorder includes remedying the disease or disorder.

In specific embodiments, treating the disease or disorder includes remedying one or more symptoms of the disease or disorder.

In specific embodiments, treating the disease or disorder includes ameliorating the disease or disorder.

In specific embodiments, treating the disease or disorder includes ameliorating one or more symptoms of the disease or disorder.

In specific embodiments, treating the disease or disorder includes improving the disease or disorder.

In specific embodiments, treating the disease or disorder includes improving one or more symptoms of the disease or disorder.

In specific embodiments, treating the disease or disorder includes stabilizing or affecting the disease or disorder.

In specific embodiments, treating the disease or disorder includes stabilizing or affecting one or more symptoms of the disease or disorder.

In specific embodiments, treating the disease or disorder includes a psychological or neurological disorder.

In specific embodiments, treating the disease or disorder includes treating obsessive compulsive disorder (OCD).

In specific embodiments, treating the disease or disorder includes treating depression.

In specific embodiments, treating the disease or disorder includes treating pain.

In specific embodiments, treating the disease or disorder includes treating irritability.

In specific embodiments, treating the disease or disorder includes treating fibromyalgia.

In specific embodiments, treating the disease or disorder includes treating post-traumatic stress disorder (PTSD).

In specific embodiments, treating the disease or disorder includes treating cluster headaches.

In specific embodiments, treating the disease or disorder includes treating paranoia.

In specific embodiments, treating the disease or disorder includes treating psychosis.

In specific embodiments, treating the disease or disorder includes treating anxiety.

In specific embodiments, treating the disease or disorder includes treating panic attacks.

In specific embodiments, treating the disease or disorder includes treating flashbacks.

In specific embodiments, treating the disease or disorder includes treating smoking addiction.

In specific embodiments, treating the disease or disorder includes treating alcohol addiction.

In specific embodiments, treating the disease or disorder includes treating cocaine addiction.

In specific embodiments, treating the disease or disorder includes treating a drug addiction.

In specific embodiments, treating the disease or disorder includes alleviating one or more symptoms of obsessive compulsive disorder (OCD).

In specific embodiments, treating the disease or disorder includes alleviating one or more symptoms of depression.

In specific embodiments, treating the disease or disorder includes alleviating one or more symptoms of pain.

In specific embodiments, treating the disease or disorder includes alleviating one or more symptoms of irritability.

In specific embodiments, treating the disease or disorder includes alleviating one or more symptoms of fibromyalgia.

In specific embodiments, treating the disease or disorder includes alleviating one or more symptoms of post-traumatic stress disorder (PTSD).

In specific embodiments, treating the disease or disorder includes alleviating one or more symptoms of cluster headaches.

In specific embodiments, treating the disease or disorder includes alleviating one or more symptoms of paranoia.

In specific embodiments, treating the disease or disorder includes alleviating one or more symptoms of psychosis.

In specific embodiments, treating the disease or disorder includes alleviating one or more symptoms of anxiety.

In specific embodiments, treating the disease or disorder includes alleviating one or more symptoms of panic attacks.

In specific embodiments, treating the disease or disorder includes alleviating one or more symptoms of flashbacks.

In specific embodiments, treating the disease or disorder includes alleviating one or more symptoms of smoking addiction.

In specific embodiments, treating the disease or disorder includes alleviating one or more symptoms of alcohol addiction.

In specific embodiments, treating the disease or disorder includes alleviating one or more symptoms of cocaine addiction.

In specific embodiments, treating the disease or disorder includes alleviating one or more symptoms of drug addiction.

In specific embodiments, the oral soft gel capsule is administered to the subject to improve creativity.

In specific embodiments, the oral soft gel capsule is administered to the subject to boost physical energy level.

In specific embodiments, the oral soft gel capsule is administered to the subject to attain emotional balance.

In specific embodiments, the oral soft gel capsule is administered to the subject to increase performance on problems-solving tasks.

In specific embodiments, the oral soft gel capsule is administered to the subject to increase emotional well-being.

In specific embodiments, the oral soft gel capsule is administered to the subject to improve the subject's mood.

In specific embodiments, the psychedelic compound is administered to the subject in a low dose.

In specific embodiments, the psychedelic compound is administered to the subject in a microdose.

In specific embodiments, a low dose of the psychedelic compound is administered to the subject, such that the low dose is sub-threshold or sub-therapeutic, insufficient to produce whole-body effects, but is high enough to allow the cellular response to be observed.

In specific embodiments, a microdose of the psychedelic compound is administered to the subject, such that the microdose is sub-threshold or sub-therapeutic, insufficient to produce whole-body effects, but is high enough to allow the cellular response to be observed.

In specific embodiments, 1-10 oral capsules a day are administered to the subject.

In specific embodiments, 1-8 oral capsules a day are administered to the subject.

In specific embodiments, 1-6 oral capsules a day are administered to the subject.

In specific embodiments, 1-4 oral capsules a day are administered to the subject.

In specific embodiments, 1-2 oral capsules a day are administered to the subject.

In specific embodiments, the capsule is administered orally (PO).

In specific embodiments, the psychedelic compound is delivered enterally.

ENUMERATED EMBODIMENTS

Specific enumerated embodiments <1.> to <44.> provided below are for illustration purposes only, and do not otherwise limit the scope of the disclosed subject matter, as defined by the claims. These enumerated embodiments encompass all combinations, sub-combinations, and multiply referenced (e.g., multiply dependent) combinations described therein.

<1.> An oral soft gel capsule comprising:
  (i) a capsule shell,
  (ii) psychedelic compound selected from the group consisting of psilocybin, psilocin, baeocystin, mescaline, LSD, ketamine, salvinorin A, ibotenic acid, muscimol, DMT, MDMA, MDEA, MDA, and combinations thereof, and
  (iii) liquid vehicle;
  wherein,
  the liquid vehicle is compatible with the capsule shell,
  the liquid vehicle effectively dissolves and/or suspends the psychedelic compound, and
  the psychedelic compound and the liquid vehicle are contained within the capsule shell.

<2.> The oral soft gel capsule of embodiment <1.>, wherein the psychedelic compound is at least one of synthetic psilocybin, synthetic psilocin and synthetic baeocystin.

<3.> The oral soft gel capsule of embodiment <1.>, wherein the psychedelic compound is at least one of psilocybin, psilocin and baeocystin, each obtained from the genera *Copelandia, Gymnopilus, Inocybe, Mycena, Panaeolus, Pholiotina, Pluteus,* or *Psilocybe.*

<4.> The oral soft gel capsule of any one of the above embodiments, wherein the psychedelic compound is present in up to 250 mg.

<5. > The oral soft gel capsule of any one of the above embodiments, wherein the psychedelic compound is present in 0.01 to 250 mg.

<6. > The oral soft gel capsule of any one of the above embodiments, wherein the psychedelic compound is at least one of psilocybin, psilocin and baeocystin, present in a combined amount of up to 100 mg.

<7. > The oral soft gel capsule of any one of the above embodiments, wherein the psychedelic compound is at least one of psilocybin, psilocin and baeocystin, present in a combined amount of up to 50 mg.

<8. > The oral soft gel capsule of any one of the above embodiments, wherein the psychedelic compound is at least one of psilocybin, psilocin and baeocystin, present in a combined amount of up to 10 mg.

<9. > The oral soft gel capsule of any one of the above embodiments, wherein the psychedelic compound is at least one of psilocybin, psilocin and baeocystin, present in a combined amount of up to 5 mg.

<10. > The oral soft gel capsule of any one of the above embodiments, wherein the psychedelic compound is at least one of psilocybin, psilocin and baeocystin, present in a combined amount of up to 1 mg.

<11. > The oral soft gel capsule of any one of the above embodiments, wherein the psychedelic compound is at least one of psilocybin, psilocin and baeocystin, present in a combined amount of 0.01 to 5 mg.

<12. > The oral soft gel capsule of any one of the above embodiments, wherein the psychedelic compound is at least one of psilocybin, psilocin and baeocystin, present in a combined amount of 0.01 to 2.5 mg.

<13. > The oral soft gel capsule of any one of the above embodiments, wherein the psychedelic compound is at least one of psilocybin, psilocin and baeocystin, present in a combined amount of 0.01 to 1 mg.

<14. > The oral soft gel capsule of any one of the above embodiments, wherein the psychedelic compound is at least one of psilocybin, psilocin and baeocystin, present in a combined amount of 0.01 to 0.5 mg.

<15. > The oral soft gel capsule of any one of the above embodiments, wherein the psychedelic compound is at least one of psilocybin, psilocin and baeocystin, present in a combined amount of 0.01 to 0.1 mg.

<16. > The oral soft gel capsule of any one of the above embodiments, wherein the psychedelic compound has a purity of at least 90 wt. % pure.

<17. > The oral soft gel capsule of any one of the above embodiments, wherein the psychedelic compound has a purity of at least 95 wt. % pure.

<18. > The oral soft gel capsule of any one of the above embodiments, wherein the psychedelic compound has a purity of at least 97.5 wt. % pure.

<19. > The oral soft gel capsule of any one of the above embodiments, wherein the psychedelic compound has a purity of at least 99 wt. % pure.

<20. > The oral soft gel capsule of any one of the above embodiments, wherein the psychedelic compound has a purity of at least 99.5 wt. % pure.

<21. > The oral soft gel capsule of any one of the above embodiments, having a content uniformity, such that among two or more samples, the amount of psychedelic compound ranges from 85% to 115%, with the standard deviation of less than or equal to 6%.

<22. > The oral soft gel capsule of any one of the above embodiments, wherein the capsule shell comprises gelatin manufactured from the collagen of animal skin and/or bone.

<23. > The oral soft gel capsule of any one of the above embodiments, wherein the capsule shell comprises hypromellose (a polymer formulated from cellulose) or pullulan (polysaccharide polymer produced from tapioca starch).

<24. > The oral soft gel capsule of any one of the above embodiments, wherein the capsule shell comprises a combination of gelatin, water, opacifier and a plasticizer, such as glycerin or sorbitol.

<25. > The oral soft gel capsule of any one of the above embodiments, wherein the liquid vehicle comprises at least one of: vegetable oil, glycerin, hydrogenated vegetable oil, lecithin, beeswax, tochopherols, polyethylene glycols (e.g., PEG 400, PEG 600), polyoxyethylene-polyoxypropylene copolymers (poloxamers), propylene glycol, and Miglyol® 812 (neutral oil, triglycerides of medium chain fatty acids).

<26. > The oral soft gel capsule of any one of the above embodiments, wherein the liquid vehicle does not comprises dimethyl isosorbide, surfactants, diethylene glycol monoethyl ether, water, or alcohol.

<27. > The oral soft gel capsule of any one of the above embodiments, wherein the liquid vehicle does comprises: no more than 0.1 wt. % dimethyl isosorbide, no more than 0.1 wt. % surfactants, no more than 0.1 wt. % diethylene glycol monoethyl ether, no more than 0.1 wt. % water, and no more than 0.1 wt. % alcohol.

<28. > The oral soft gel capsule of any one of the above embodiments, exhibiting a high stability such that at least 90 wt. % of the psychedelic compound remains in the oral soft gel capsule, under accelerated stability conditions of ≥40° C., relative humidity (RH) 75±5%, over a period of time of ≥3 months.

<29. > The oral soft gel capsule of any one of the above embodiments, exhibiting a high stability such that at least 95 wt. % of the psychedelic compound remains in the oral soft gel capsule, under accelerated stability conditions of ≥40° C., relative humidity (RH) 75±5%, over a period of time of ≥3 months.

<30. > The oral soft gel capsule of any one of the above embodiments, exhibiting a high stability such that at least 97.5 wt. % of the psychedelic compound remains in the oral soft gel capsule, under accelerated stability conditions of ≥40° C., relative humidity (RH) 75±5%, over a period of time of ≥3 months.

<31. > The oral soft gel capsule of any one of the above embodiments, exhibiting a high stability such that at least 99 wt. % of the psychedelic compound remains in the oral soft gel capsule, under accelerated stability conditions of ≥40° C., relative humidity (RH) 75±5%, over a period of time of ≥3 months.

<32. > The oral soft gel capsule of any one of the above embodiments, further including a preservative.

<33. > The oral soft gel capsule of any one of the above embodiments, further including an opacifier.

<34. > The oral soft gel capsule of any one of the above embodiments, further including a flavorant.

<35. > The oral soft gel capsule of any one of the above embodiments, further including a colorant.

<36. > A method of treating in a subject a disease or disorder ameliorated by a psychedelic compound, the method comprising orally administering to the subject an oral soft gel capsule of any one embodiments <1. > to <35. >, in an amount and for a period of time sufficient to effectively treat the disease or disorder.

<37. > A method of treating in a subject a psychological or neurological disorder, the method comprising orally administering to the subject an oral soft gel capsule of any one embodiments <1.> to <35.>, in an amount and for a period of time sufficient to effectively treat the psychological or neurological disorder.

<38.> The method of any one of embodiments <36.> to <37.>, wherein the psychological or neurological disorder comprises at least one of obsessive compulsive disorder (OCD), depression, pain, irritability, fibromyalgia, post-traumatic stress disorder (PTSD), cluster headaches, paranoia, psychosis, anxiety, panic attacks, flashbacks, smoking addiction, alcohol addiction, and cocaine addiction.

<39.> A method comprising orally administering to a subject an oral soft gel capsule of any one embodiments <1.> to <35.>, wherein the oral soft gel capsule comprises a low dose or microdose of the psychedelic compound.

<40.> The method of embodiment <39.>, wherein the low dose or microdose of the psychedelic compound is sub-threshold or sub-therapeutic insufficient to produce whole-body effects, but is high enough to allow the cellular response to be observed.

<41.> The method of any one of embodiments <39.> to <40.>, which is a method to improve creativity, boost physical energy level, attain emotional balance, increase performance on problems-solving tasks, to treat anxiety, to treat depression, to treat addiction, or any combination thereof.

<42.> The method of any one of embodiments <39.> to <41.>, which is a method to treat at least one of obsessive compulsive disorder (OCD), pain, irritability, fibromyalgia, post-traumatic stress disorder (PTSD), cluster headaches, paranoia, psychosis, anxiety, panic attacks, flashbacks, smoking addiction, alcohol addiction, and cocaine addiction.

<43.> The method of any one of embodiments <36.> to <42.>, wherein 1-5 oral capsules are orally administered a day.

<44.> The method of any one of embodiments <36.> to <43.>, wherein the psychedelic compound is delivered enterally.

The invention claimed is:

1. A method of treating anxiety in a subject, the method comprising orally administering to a subject in need or at risk thereof an oral soft gel capsule comprising:
   (i) a capsule shell formed from gelatin and at least one of vegetable starch, tapioca starch, carrageenan, potato starch, cassava starch, cornstarch, and arrowroot;
   (ii) a psychedelic compound comprising at least one of psilocybin, psilocin, and baeocystin; and
   (iii) liquid vehicle comprising at least one of glycerin, beeswax, tocopherols, polyoxyethylene-polyoxypropylene copolymers, and Caprylic/Capric Triglyceride;
   wherein,
   the psilocybin, psilocin baeocystin, or combination thereof is present in a combined amount of 0.01 to 5 mg,
   the psilocybin, psilocin, baeocystin, or combination thereof has a purity of at least 99 wt. % pure,
   the psilocybin, psilocin, baeocystin, or combination thereof is obtained from the genera *Copelandia, Gymnopilus, Inocybe, Mycena, Panaeolus, Pholiotina, Pluteus,* or *Psilocybe,*
   the liquid vehicle is compatible with the capsule shell;
   the liquid vehicle effectively dissolves and/or suspends the psychedelic compound; and
   the psychedelic compound and the liquid vehicle are contained within the capsule shell.

2. The method of claim 1, wherein the anxiety is associated with at least one of obsessive compulsive disorder (OCD), pain, irritability, fibromyalgia, post-traumatic stress disorder (PTSD), cluster headaches, paranoia, psychosis, anxiety, panic attacks, flashbacks, smoking addiction, alcohol addiction, and cocaine addiction.

3. The method of claim 1, wherein 1-5 oral soft gel capsules are orally administered a day.

4. The method of claim 1, wherein the psilocybin, psilocin, baeocystin, or combination thereof is delivered enterally.

5. The method of claim 1, wherein the psilocybin, psilocin, baeocystin, or combination thereof is present in a combined amount of 0.05 to 2.5 mg.

6. The method of claim 1, wherein the psilocybin, baeocystin, or combination thereof is present in a combined amount of 0.05 to 1 mg.

7. The method of claim 1, wherein the psilocybin, baeocystin, or combination thereof is present in a combined amount of 0.1 to 1 mg.

8. The method of claim 1, wherein the liquid vehicle further comprises at least one of vegetable oil, hydrogenated vegetable oil, lecithin, polyethylene glycols, and propylene glycol.

9. The method of claim 1, wherein the liquid vehicle comprises less than 0.1 wt. % of each of dimethyl isosorbide, surfactants, diethylene glycol monoethyl ether, water, and alcohol.

10. The method of claim 1, wherein the oral soft gel capsule exhibits a high stability such that at least 90 wt. % of the psilocybin, psilocin, baeocystin, or combination thereof remains in the oral soft gel capsule, under accelerated stability conditions of ≥40° C., relative humidity (RE) 75±5%, over a period of time of ≥3 months.

11. The method of claim 1, wherein the oral soft gel capsule further comprises a preservative.

12. The method of claim 1, wherein the oral soft gel capsule further comprises an opacifier.

13. The method of claim 1, wherein the oral soft gel capsule further comprises a flavorant.

14. The method of claim 1, wherein the oral soft gel capsule further comprises a colorant.

15. The method of claim 1, wherein the oral soft gel capsule comprises a capsule shell that, when empty, blocks at least 99% of U light from transmitting therethrough.

16. The method of claim 1, wherein the capsule shell is further formed from a plasticizer glycerin, or sorbitol, or combination thereof.

17. The method of claim 1, wherein the capsule shell is further formed from the solvent water.

18. The method of claim 1, wherein the capsule shell is further formed from cellulose, hypromellose, or combination thereof.

19. The method of claim 1, wherein the the gelatin of capsule shell is further formed from collagen of animal skin and/or bone.

20. A method of treating anxiety in a subject, the method comprising orally administering to a subject in need or at risk thereof an oral soft gel capsule comprising:
   (i) a capsule shell formed from gelatin and at least one of vegetable starch, tapioca starch, carrageenan, potato starch, cassava starch, cornstarch, and arrowroot;
   (ii) a psychedelic compound comprising at least one of psilocybin, psilocin and baeocystin; and
   (iii) liquid vehicle comprising at least one of glycerin, beeswax, tocopherols, polyoxyethylene-polyoxypropylene copolymers, and Caprylic/Capric Triglyceride;
   wherein,
   the psychedelic compound has a purity of at least 90 wt. % pure, the liquid vehicle is compatible with the capsule shell;
the liquid vehicle effectively dissolves and/or suspends the psychedelic compound; and
the psychedelic compound and the liquid vehicle are contained within the capsule shell.

21. The method of claim 20, wherein the psychedelic compound is present in up to 250 mg.

22. The method of claim 20, wherein the psychedelic compound comprises at least one of psilocybin, psilocin, and baeocystin and is present in a combined amount of up to 100 mg.

23. The method of claim 22, wherein the psychedelic compound is present in up to 35 wt. % of the liquid vehicle.

24. The method of claim 20, wherein the psychedelic compound is present in up to 5 wt. % of the liquid vehicle.

25. The method of claim 20, wherein t the psychedelic compound has a purity of at least 95 wt. % pure.

26. The method of claim 20, wherein t the psychedelic compound has a purity of at least 97.5 wt. % pure.

* * * * *